US006471975B1

(12) United States Patent
Banovetz et al.

(10) Patent No.: US 6,471,975 B1
(45) Date of Patent: Oct. 29, 2002

(54) MICROSPHERES AS A DELIVERY VEHICLE FOR BIO-ACTIVE AGENTS USEFUL IN AGRICULTURAL APPLICATIONS

(75) Inventors: John P. Banovetz, Minneapolis, MN (US); Kent E. Nielsen, Dorchester (CA); Kai Li, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 12 days.

(21) Appl. No.: 09/071,567

(22) Filed: May 1, 1998

(51) Int. Cl.$^7$ .............................................. A01N 25/28
(52) U.S. Cl. ...................... 424/408; 424/409; 424/417; 424/418; 424/419; 424/420; 424/84; 424/489; 424/490; 424/497; 504/113; 514/918; 514/919; 514/920
(58) Field of Search ................... 424/405, 408, 424/417–420, 489, 490, 497, 501, 84; 504/113, 116, 118, 150, 162, 174, 184, 189; 514/918–920; 428/402.2; 264/4, 4.3–4.7

(56) References Cited

U.S. PATENT DOCUMENTS 3,691,140 A  9/1972  Silver (List continued on next page.)

FOREIGN PATENT DOCUMENTS

| EP | 0 227 987 | 7/1987 |
|----|-----------|--------|
| WO | WO 81/02505 | 9/1981 |
| WO | WO 92/10285 | 6/1992 |
| WO | WO 95/13698 | 5/1995 |
| WO | WO 96/01048 | 1/1996 |
| WO | WO 96/01280 | 1/1996 |
| WO | WO 97/46633 | 12/1997 |
| WO | WO 97/46634 | 12/1997 |
| WO | WO 98/17481 | 4/1998 |
| WO | WO 98/44912 | 10/1998 |

OTHER PUBLICATIONS

Heya, Toshiro et al. "Controlled Release of Thyrotropin Releasing Hormone from Microspheres: Evaluation of Release Profiles and Pharmacokinetics after Subcutaneous Administration", Journal of Pharmaceutical Sciences, Jun. 1994, vol. 83, No. 6, pp. 798–801.

"Interaction Between Nicardipine Hydrochloride and Polymeric Microspheres for a Controlled Release System", Elsevier International Journal of Pharmaceutics 140 (1996) 145–154.

Hall, D. R., Marrs, G. J. *Insect Pheromones in Plant Protection*, Jutsum, A. R. and Gordon, R. F. S. eds, John Wiley and Sons, 1989, p. 220.

*Primary Examiner*—Neil S. Levy
(74) *Attorney, Agent, or Firm*—Carolyn V. Peters (57) ABSTRACT

A plurality of releasably loaded elastomeric microspheres comprising a plurality of elastomeric microspheres loaded with at least one releasable agriculturally active agent within the optical boundaries of the elastomeric microspheres and post-polymerization addition and in-situ polymerization processes for preparing the releasably loaded elastomeric microspheres are also provided.

8 Claims, 1 Drawing Sheet

U.S. PATENT DOCUMENTS

| | | |
|---|---|---|
| 3,928,546 A | 12/1975 | Cardarelli |
| 4,166,152 A | 8/1979 | Baker et al. |
| 4,244,836 A * | 1/1981 | Frensch et al. ............. 252/216 |
| 4,353,962 A | 10/1982 | Himel et al. |
| 4,415,615 A | 11/1983 | Esmay et al. |
| 4,495,318 A | 1/1985 | Howard |
| 4,690,825 A | 9/1987 | Won |
| 4,707,355 A * | 11/1987 | Wilson ........................ 424/84 |
| 4,786,696 A | 11/1988 | Bohnel |
| 4,968,562 A | 11/1990 | Delgado |
| 4,988,467 A | 1/1991 | Holdsworth et al. |
| 4,994,322 A | 2/1991 | Delgado |
| 5,045,569 A | 9/1991 | Delgado |
| 5,053,436 A | 10/1991 | Delgado |
| 5,118,750 A | 6/1992 | Silver et al. |
| 5,215,818 A | 6/1993 | Silver et al. |
| 5,286,493 A | 2/1994 | Oshlack et al. |
| 5,460,817 A * | 10/1995 | Langley et al. ............. 424/408 |
| 5,502,108 A | 3/1996 | Silver et al. |
| 5,503,839 A | 4/1996 | Saguchi et al. |
| 5,508,313 A | 4/1996 | Delgado et al. |
| 5,571,617 A | 11/1996 | Cooprider et al. |
| 5,603,961 A | 2/1997 | Suzuki et al. |
| 5,639,476 A | 6/1997 | Oshlack et al. |

\* cited by examiner

*Figure 1*

MICROSPHERES AS A DELIVERY VEHICLE FOR BIO-ACTIVE AGENTS USEFUL IN AGRICULTURAL APPLICATIONS

TECHNICAL FIELD

This invention relates to elastomeric microspheres and their uses in delivery and controlled release of agriculturally active agents, particularly insect pheromones.

BACKGROUND OF INVENTION

Pheromones are chemical compounds that influence specific patterns of behavior in a particular type of animal species. The use of pheromones to control insect populations offers several advantages over other methods of insect control. Unlike pesticides, pheromones are species specific; no major disruption or threat to the overall environment occurs. Also, insect populations respond to low levels of pheromones, so the threat of a high concentration of toxins or contaminates can be mitigated. Pheromones can effectively control various insect populations such as the Codling Moth, Grape Berry Moth, Pink Boll Worm, Tomato Pinworm and Spotted Fireworm.

Microencapsulation of agriculturally active agents demonstrates several advantages over other delivery methods. Microencapsulated materials should be safer to handle, reduce the total amount of active material needed, and reduce the potential for leaching while maintaining biological activity. Also, microencapsulated materials enable site-specific delivery of the active material. Site-specific delivery reduces the effective dose while increasing the therapeutic effect of the active material.

There are a number of techniques available in the art for microencapsulating agriculturally active materials. Solvent evaporation, interfacial polymerization, emulsion polymerization or drying techniques represent a few of these methods. Limitations exist for all these methodologies. Solvent evaporation or spray drying techniques typically incorporate organic. solvents. Interfacial polymerization can be inhibited by active materials that contain reactive functionalities. For example, alcohols are difficult to encapsulate by existing interfacial methods because they can react rapidly with electrophilic monomers (see e.g., Hall, D. R., Marrs, G. J. Insect Pheromones in Plant Protection, Jutsum, A. R. and Gordon, R. F. S. eds, John Wiley and Sons, 1989, p. 220). Conventional emulsion polymerization techniques generally fail to adequately incorporate water insoluble materials. The term "conventional emulsion polymerization techniques" refers to heterogeneous polymerization methods utilizing a water-soluble initiator and relying on monomer diffusion.

Several approaches have been described to microencapsulate agriculturally active agents. Typically, polymers with a high glass transition temperature are used. For example, poly(α-methyl stryene), and poly(methyl methacrylate) have been used to affect release of herbicides such as atrazine, metribuzin, alachlor, and metolachlor. However, herbicides combined with poly(α-methyl stryene), and poly (methyl methacrylate) failed to show consistent, high activity.

Thus, a need exists for alternative techniques for encapsulating agriculturally active agents that may be used to prepare releasably encapsulated agriculturally active agents.

SUMMARY OF INVENTION

Briefly, in one aspect of the present invention, a releasably loaded elastomeric microsphere is provided comprising a releasable agriculturally active agent within the boundary of the elastomeric microsphere. Releasable agriculturally active agents can include for example, pheromones, herbicides, pesticides and the like. These agents may or may not be soluble in polymerized elastomeric microspheres or in their monomeric precursors. Uniquely, the agriculturally active agent can be incorporated into the microsphere using either a post polymerization addition process or an in-situ addition process.

Advantageously, loading microspheres with a releasable agriculturally active agent within the boundaries of the microspheres provides a unique delivery device that can be fashioned to provide characteristics that are application specific. Examples of such delivery devices include but are not limited to substrates (such as tapes, sheets of material and the like) coated with the releasably loaded elastomeric microspheres; sprayable dispersions; or suspensions of these elastomeric microspheres and the like.

Another advantage is that elastomeric microspheres provide a unique way to modify release rates because polymer matrices can be modified to influence release rates. Also, the use of releasably loaded elastomeric microspheres offers the opportunity to create tacky particles capable of adhering to a substrate and provide delivery of agriculturally active agents. Tacky releasably loaded elastomeric microspheres eliminate the need to formulate conventionally encapsulated agriculturally active agents with sticky latex polymers to adhere encapsulated materials to a target substrate. Such tacky releasably loaded elastomeric microspheres can be used to deliver agriculturally active agents to difficult places, such as forest canopies, with sustained lasting power to environmental forces (wind, rain, etc.). The agriculturally active agent that is enclosed within the releasably loaded elastomeric microspheres may be either a liquid or a solid. Solid agriculturally active agents are first suspended in the monomer mixture or a solvent, but may be contained in the microsphere in the solid form due to either polymerization and/or evaporation of the solvent. Liquid agriculturally active agents may be added to the monomer mixture or added directly to the microsphere.

Finally, the releasably loaded elastomeric microspheres of the present invention can be formulated into sprayable mixtures, either as dispersions or suspensions, allowing for easy application and handling.

In another aspect of the present invention, the releasably loaded elastomeric microspheres can be prepared using a post polymerization addition process, wherein polymerized elastomeric microspheres are blended with a releasable agriculturally active agent or mixture of agents under such conditions to cause the releasable agriculturally active agent to be absorbed within the boundaries of the elastomeric microspheres. The process for preparing such releasably loaded elastomeric microspheres comprises the steps of:

(a) providing polymerized elastomeric microsphere precursors;

(b) blending the polymerized elastomeric microsphere precursors with a releasable agriculturally active agent or mixture of agents, wherein the releasable agriculturally active agent or mixture of agents is optionally dissolved in a solvent and such that the releasable agriculturally active agent is absorbed within the boundaries of the polymerized elastomeric microsphere precursors and;

(c) optionally, removing the solvent.

An alternative in-situ addition process for preparing releasably loaded elastomeric microspheres comprises the steps of:

(a) forming an oil phase comprising at least one oil soluble monomer, an oil soluble initiator and a releasable agriculturally active agent or a portion of the releasable agriculturally active agent in a water phase comprising at least one suspension stabilizer or surfactant;

(b) initiating polymerization of the oil phase in the water phase; and (c) optionally, adding remaining releasable agriculturally active agent.

In this application:

"boundary or boundaries" mean the outside limits of the elastomeric microspheres' polymeric structure;

"elastomeric" means amorphous or noncrystalline materials that can be stretched and that will retract rapidly to substantially their original dimensions upon release of the force;

"agriculturally active" means a composition that produces a response in cultivated soil, crops, and/or livestock;

"releasable" means when the elastomeric microsphere is placed in its intended environment of use, an agriculturally effective amount of the agriculturally active agent diffuses out of the microsphere;

"releasably loaded" means all or a portion of an agriculturally active agent is contained within the optical boundaries of the elastomeric microspheres in an amount sufficient to diffuse out of the microsphere;

"solvent" means conventional organic liquids generally used in the industry that include, for example, toluene, heptane, ethyl acetate, methyl ethyl ketone, acetone, and mixtures thereof and does not include water;

"partially water miscible" means the solubility of the compound in water is less than 98% but greater than 0.5% by weight, that is, if one gram of the compound is put in 100 grams of water, 0.98 grams would dissolve; and "water immiscible" means the solubility of the compound in water is less than 0.5% by weight.

DESCRIPTION OF THE PREFERRED EMBODIMENTS

Figure 1:
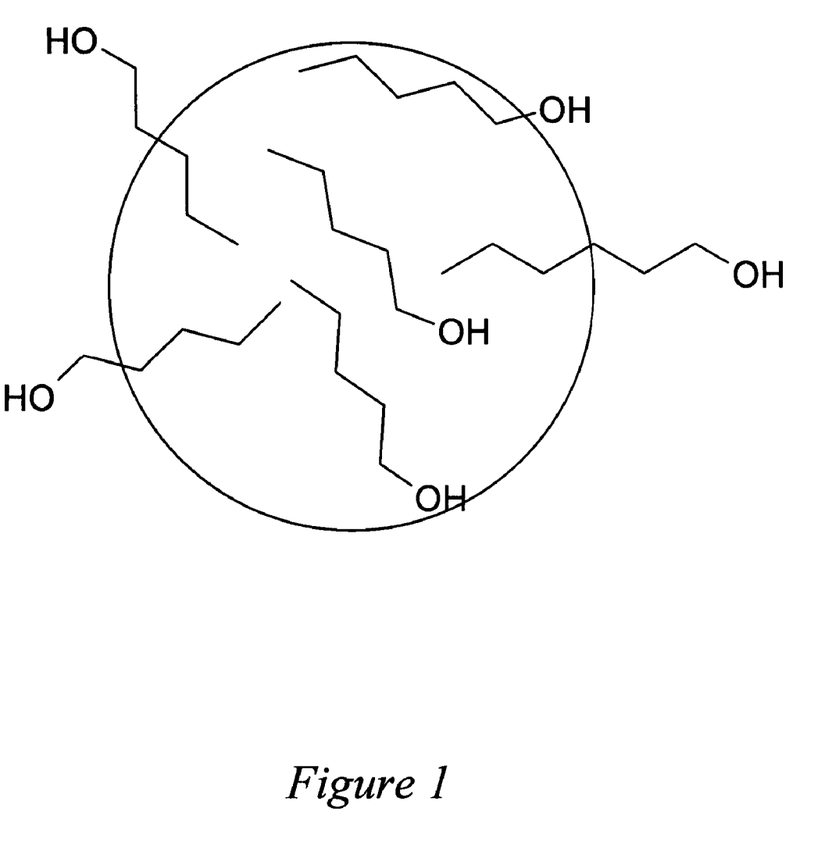
FIG. 1 is a graphical representation of a agriculturally loaded microsphere according to the present invention."

It has been discovered that releasably loaded elastomeric microspheres can be used as a delivery agent for agriculturally active agents. When the microspheres are combined with active agents, either prior to or after polymerization, compositions capable of controlled release of the active agent are produced.

Elastomeric Microspheres

The following disclosure regarding elastomeric microspheres applies both to releasably loaded elastomeric microspheres and the polymerized elastomeric microsphere precursors described herein.

Elastomeric microspheres can be solid or hollow and are generally crosslinked to an extent such that the microspheres remain in particle form throughout processing and use. Typically, elastomeric microspheres are prepared via suspension polymerization of one or more free radically polymerizable monomers in the presence of surfactants and/or suspension stabilizers. Choice of surfactants and/or suspension stabilizers and their specific combinations with specific monomers can determine suspension stability, desired particle morphology, performance characteristics, such as whether or not the elastomeric microspheres are tacky or tack free. Tacky elastomeric microspheres have been used in repositionable pressure sensitive adhesive applications and there are numerous references discussing preparation and/or use of these elastomeric microspheres. The term "repositionable" refers to the ability to be repeatedly adhered to and removed from a substrate without substantial loss of adhesion capability.

Various copolymerizable monomeric components may be added to the free radically polymerizable monomers, suspension stabilizers and/or surfactants to modify the properties of the suspension polymerized microspheres. Nitrogen-containing polar monomers may also be added to acid-free acrylate suspension polymerization mixtures to form elastomeric microspheres containing multiple internal voids. Polar comonomers having no dissociable protons or low levels of dissociable protons, when used along with particular surfactant and polymeric stabilizer combinations, can be added to suspension polymerizable formulations to yield microspheres having enhanced adhesive properties, while maintaining their repositionable and self cleaning qualities against a variety of surfaces.

Copolymerizable or otherwise incorporated oligomeric and polymeric additives can also be employed in suspension polymerized microspheres to alter properties, such as adhesion, release rates and other performance characteristics of the elastomeric microspheres. Hydrophilic oligomers and polymers can be included in suspension polymerizable microsphere formulations to provide improved microsphere stability and, in some formulations, water dispersibility. Water insoluble polymeric components can also be incorporated into microspheres by suspension polymerization of alkyl(meth)acrylate and other comonomers in the presence of such polymeric components. Such incorporation allows for the inclusion of water insoluble polymer components into microspheres that could not typically occur under standard free radical suspension polymerization conditions. Another advantage of this water insoluble polymer incorporation is to modify the physical properties, such as adhesion and release rates of the microspheres.

Elastomeric microspheres of the present invention can be prepared by suspension, dispersion, direct emulsion and modified emulsion techniques. Preferably, the elastomeric microspheres are prepared according to the suspension polymerization methods described in, for example, U.S. Pat. Nos. 3,691,140; 4,166,152; 4,495,318; 4,786,696; 4,988,467; 5,045,569; 5,508,313; and 5,571,617 and PCT Publications WO96/01280, WO97/46633, and WO97/46634, the disclosures of which are incorporated herein by reference.

Elastomeric microspheres are preferably prepared using suspension polymerization techniques. These techniques offer several advantages over other methodologies, including: (1) the elimination of solvent, (2) low viscosity dispersion, (3) a controlled particle size, and (4) controlled particle morphology. Suspension polymerization also allows for versatile manufacturing methods. The releasable agriculturally active agent may be added to either the monomer mixture before or during polymerization or to the polymerized elastomeric microsphere precursors.

Specifically, suspension polymerization offers several advantages over interfacial polymerization for incorporation of the releasable agriculturally active agent or mixture of such agents. First, suspension polymerization is capable of incorporating a wider concentration range of active material. Second, suspension polymerization may occur at a higher solids content. Third, suspension polymerization is typically a free radical process and can tolerate agriculturally active agents that contain reactive functionalities (alcohols, amines, aldehydes, etc.). For example, alcohols are difficult to encapsulate by existing interfacial methods because they react rapidly with electrophilic monomers (see e.g., Hall, D. R., Marrs, G. J. Insect Pheromones in Plant Protection, Jutsum, A. R. and Gordon, R. F. S. eds, John Wiley and Sons, 1989, p. 220). Finally, suspension techniques provide for greater control over particle size and particle size distribution.

In preferred suspension polymerization methods, elastomeric microspheres can be prepared by forming an oil phase comprising oil soluble free-radically polymerizable monomers, optionally also containing free radically polymerizable polar comonomers, and an oil soluble free radical initiator in an water phase that comprises an aqueous medium having at least one suspension stabilizer or surfactant. Depending on the types and amounts of monomer and comonomers, crosslinking agents, stabilizers, surfactants, reaction conditions, and other composition and process alternatives employed, these microspheres can be hollow (that is, having at least one internal void or cavity) or solid (that is, having no internal voids or cavities); tacky or tack-free; water or solvent dispersible; lightly or highly crosslinked; and a range of diameters (from about 0.5 to 300 micrometers) and polymeric morphologies. Preferred elastomeric microspheres are acrylate or vinyl ester microspheres and may be used as a mixture of acrylate and vinyl ester microspheres.

(Meth)acrylic acid esters monomers used in elastomeric acrylate microspheres are monofunctional unsaturated (meth)acrylate esters of non-tertiary alkyl alcohols. The alkyl groups of these alcohols preferably contain from 4 to 14 (more preferably 4 to 10) carbon atoms and as homopolymers have glass transition temperatures ($T_g$) lower than about −20° C. Examples of useful monomers included sec-butyl acrylate, n-butyl acrylate, isoamyl acrylate, 2-methylbutyl acrylate, 4-methyl-2-pentyl acrylate, 2-ethylhexylacrylate, isooctyl acrylate, isononyl acrylate, isodecyl methacrylate, isodecyl acrylate, dodecyl acrylate, tetradecyl acrylate and mixtures thereof. Particularly preferred are n-butyl acrylate, sec-butyl acrylate, isoamyl acrylate, 2-ethylhexyl acrylate, isooctyl acrylate, isononyl acrylate, isodecyl acrylate, and mixtures thereof. Of these, isooctyl acrylate and 2-ethylhexyl acrylate are the most preferred.

Vinyl ester monomers useful for providing the elastomeric vinyl ester microspheres are unsaturated vinyl ester derived from linear or branched carboxylic acids having 1–14 (preferably 7 to 12) carbon atoms (not counting the carboxyl carbon atom) and as homopolymers have glass transition temperatures ($T_g$) lower than about −20° C. Suitable vinyl ester monomers include vinyl propionate, vinyl pelargonate, vinyl hexanoate, vinyl caprate, vinyl 2-ethyihexanoate, vinyl octanoate, vinyl decanoate, vinyl laurate, and mixtures thereof. Particularly preferred are vinyl caprate, vinyl 2-ethylhexonate, vinyl laurate, and mixtures thereof.

(Meth)acrylate ester or other vinyl monomers which, as homopolymers, have glass transition temperatures higher than about −20° C., e.g. ethyl acrylate, tert-butyl acrylate, isobornyl acrylate, butyl methacrylate, vinyl acetate, acrylonitrile, mixtures thereof, and the like, may be used in conjunction with one or more of the (meth)acrylate and vinyl ester monomers provided that the glass transition temperature of the resulting microspheres are below about −0° C.

Elastomeric acrylate or vinyl ester microspheres useful in the present inventions may further comprise a free radically polymerizable polar comonomer copolymerizable with (meth)acrylic acid ester or vinyl ester monomer. The free radically polymerizable polar comonomers may be added to improve or modify the cohesive strength, storage stability, release rates, adhesion to polar surfaces, and glass transition temperature of the microspheres. It is preferred that the polar monomer be incorporated in an amount of no more than about 1 to 20 parts by weight.

In addition to their copolymerizability with the (meth)acrylic acid ester or vinyl ester monomer, the free radically polymerizable polar comonomers are monomers that are both oil and water soluble and include one of the following polar substituents: amide, nitrile, hydroxyl, and carboxylic acid (including acid salt) groups. Suitable polar monomers included monoolefinic monocarboxylic acids, monoolefinic dicarboxylic acids, salts thereof, acrylamides, N-substituted acrylamides, N-vinyl lactams, and mixtures thereof. Representative examples of these classes of useful polar monomers include acrylic acid, methacrylic acid, itaconic acid, crotonic acid, maleic acid, fumaric acid, sulfoethyl methacrylate, N-vinyl pyrrolidone, N-vinyl caprolactam, acrylamide, t-butyl acrylamide, dimethylamino ethyl acrylamide, N-octyl acrylamide, hydroxy ethyl acrylate, and hydroxy ethyl methacrylate. Ionic monomers (a class of polar monomers) such as sodium methacrylate, sodium styrene sulfonate, ammonium acrylate, sodium acrylate, trimethylamine p-vinyl benzimide, N,N-dimethyl-N-(beta-methoxy-ethyl)ammonium propionate betaine, trimethylamine methacrylamide, 1,1-dimethyl-1-(2,3-dihydrooxylpropyl)amine methacrylamide, and mixtures thereof are also useful. Particularly preferred are acrylic acid, sodium acrylate, ammonium acrylate, N-vinyl pyrrolidone, and mixtures thereof.

The elastomeric microspheres useful in the invention may also contain a multifunctional free-radically polymerizable crosslinking agent. Such crosslinking agents can enhance the cohesive strength and solvent insolubility of the individual microspheres by internally crosslinking them. "Multifunctional" refers to crosslinking agents that possess two or more free-radically polymerizable olefinically unsaturated groups. Useful multifunctional crosslinking agents include (meth)acrylic esters of diols (e.g., butanediol), triols (e.g., glycerol), and tetrols (e.g., pentaerythritol); polymeric multifunctional (meth)acrylates (e.g., poly(ethylene oxide) diacrylate and poly(ethylene oxide) dimethacrylate); polyvinylic compounds (e.g., substituted and unsubstituted divinylbenzene); difunctional urethane acrylates; and mixtures thereof.

When a crosslinking agent is employed, it is typically used at a level of up to about 0.15 equivalent weight percent. Above about 0.15 equivalent weight percent, the microspheres tend to lose their pressure sensitive adhesive qualities and eventually become non-tacky to the touch at room temperature. Non-tacky and tacky microsphere are useful in this invention. Addition of the agriculturally active agent may alter the properties of the elastomeric microspheres through plasticization or tackification. The level of crosslinking agent may be altered and changed to counteract the effects of the agriculturally active agent on particle rheology.

The "equivalent weight percent" of a given compound is defined as the number of equivalents of that compound divided by the total number of equivalents of the free radically polymerizable unsaturation in the total microsphere composition. An equivalent is the number of grams divided by the equivalent weight. The equivalent weight is defined as the molecular weight divided by the number of polymerizable groups in the monomer (in the case of those monomers with only one polymerizable group, equivalent weight=molecular weight).

Crosslinking may also be controlled with the use of chain transfer agents. Useful chain transfer agents are those that are normally suited for free radical polymerization of acrylates. The chain transfer agents useful in the practice of the invention include, but are not limited to, carbon tetrabromide, n-dodecyl mercaptan, isooctylthiolglycolate, and mixtures thereof. If used, the chain transfer agent(s) are present in the amounts from 0.001 to 1 percent by weight of the total polymerizable composition.

Useful oil soluble free radical initiators are those that are normally suitable for free radical polymerization of acrylate or vinyl ester monomers and which are oil soluble and of very low solubility in water, typically less than 1 g/100 g water at 20° C. Examples of such free radical initiators include azo compounds, hydroperoxides, peroxides, benzophenone, benzoin ethyl ether, 2,2-dimethoxy-2-phenyl acetophenone and the like. Initiators generally used in an amount ranging from about 0.01 percent up to about 10 percent by weight of the total polymerizable composition, preferably up to about 5 percent. Furthermore, one or more initiators, that is a mixture of initiators may be used.

Use of a substantially water soluble polymerization initiator, such as those generally used in emulsion polymerizations, causes formation of substantial amounts of latex. During suspension polymerization, any significant formation of latex is undesirable because of the extremely small particle size.

The elastomeric acrylate or vinyl ester microspheres tend to be bead or pearl shaped, although they may be more spheroidal. Typically, they have a volume average diameter of about 0.5 to 300 microns (more preferably, about 1 to 100 microns). Hollow microspheres contain one or more voids; i.e., one or more spaces completely within the walls of the polymerized microsphere. Typically the hollow portion is less than 100 microns in average diameter.

If hollow microspheres are desired they may be obtained either by using a "two step" process as described in U.S. Pat. No. 4,968,562 or by using a "one step" process as described in U.S. Pat. No. 5,053,436.

Solid pressure sensitive adhesive microspheres may be prepared via the suspension polymerization techniques that use ionic or nonionic emulsifiers in an amount sufficient to generate the necessary particle and is generally near the critical micelle concentration.

Each suspension polymerization method (whether producing hollow or solids microspheres) may be modified by withholding the addition of all or some of the free-radically polymerizable polar comonomer until after the polymerization of the oil phase (meth)acrylic acid ester or vinyl ester has been initiated. In this instance, however, these components must be added to the polymerizing mixture before 100% conversion of the (meth)acrylic acid ester or vinyl ester monomer. Similarly, a multifunctional free-radically polymerizable crosslinking agent (if used) can be added at any time before 100% conversion to polymer of the monomers of the microsphere composition. Preferably the crosslinking agent is added before initiation occurs.

Elastomeric microspheres consist of polymers having low glass transition temperatures. Further, elastomeric microspheres may be tacky or tack-free and may possess solid or hollow morphology. The microspheres may incorporate pendant hydrophilic polymeric or oligomeric moieties. The microspheres may range in size from 0.5 micrometers to 300 micrometers.

Agriculturally Active Agents

Agriculturally active agents that may be used in this invention include water immiscible or partly miscible compounds. The compounds may be highly functionalized and include such functional groups as aldehydes, alcohols, epoxy compounds, ethers or ketones. Agriculturally active agents useful with this invention include but are not limited to: insecticides, herbicides, fungicides, bactericides, pheromones and other pesticides, and insect repellents. Preferred agriculturally active agents include insect repellents such as citronella and insect pheromones. Particularly preferred compounds are insect pheromones. In the notation used below to describe the structure of the pheromones, the type (E or Z) and the position of the double bond or bonds are given first, the number of carbon atoms in the chain is given next and the nature of the end group is given last. To illustrate, the pheromone Z-10 C19 aldehyde has the structure:

Pheromones may in fact be mixtures of compounds with one component of the mixture predominating, or at least being a significant component. Mentioned as examples of partially water miscible significant or predominant components of insect pheromones, with the target species in brackets, are the following: E/Z-11 C14 aldehyde (Eastern Spruce Budworm), Z-10 C19 aldehyde (Yellow Headed Spruce Sawfly), Z-11 C14 alcohol (Oblique Banded Leafroller), Z-8 C12 alcohol (Oriental Fruit Moth) and E, E-8,10 C12 alcohol (Codling Moth).

An example of a ketone that is a pheromone is E- or Z-7-tetradecen-2-one, which is effective with the Oriental Beetle. An ether that is not a pheromone but is of value is 4-allylanisole, which can be used to render pine trees unattractive to the Southern Pine Beetle.

The compositions of the invention are made by addition of the agriculturally active agent to the monomer mixture or monomer dispersion prior to polymerization (in-situ addition process). Or the agriculturally active agent may be added directly to the microsphere dispersion following polymerization.

The agriculturally active agents are present in concentrations necessary to be effective while not hindering the stability or polymerization of the microspheres. Furthermore, a single agriculturally active agent may be used, as well, as a mixture of such agents. Typically, such concentrations are present in amounts of at least 1% by weight of the releasably loaded elastomeric microspheres, preferably in the range of 1 to 20%, most preferably in the range of 1 to 10%. Generally, less than 1% by weight of the releasably loaded elastomeric microspheres are ineffective, although this may vary with the agriculturally active agent used and the weight percents may be as low at 100 ppm level. The agriculturally active agent may act as a plasticizer or tackifying agent as a result of its association with the microsphere and therefore levels of crosslinking agents may need to be adjusted. If the agriculturally active agent is present in the monomer dispersion, that is, it is used in the in-situ addition process, the agriculturally active agent must not inhibit to the extent that polymerization is halted, although the agriculturally active agent may work to retard the polymerization.

Other adjuvants can be included in the compositions in amounts needed to effect the desired properties as long as they do not affect the polymerization or the desired end properties or both. Furthermore, such adjuvants may be added to the microspheres during polymerization before mixing. Useful adjuvants include dyes, pigments, fillers, UV protectants, and coupling agents.

The releasably loaded elastomeric microspheres are useful in the preparation of coated articles, such as adhesive tapes and coated sheets. Tapes typically have narrow widths in comparison to length. Sheets typically have substantially equal lengths and widths and may generally be prepared in the same manner as tapes. The tapes can be prepared as transfer tapes in which the releasably loaded elastomeric microspheres are typically provided on a liner coating on both sides with a release coating. The tapes can also be prepared by having the releasably loaded elastomeric microspheres permanently adhered to the backing. Tapes with the releasably loaded elastomeric microspheres permanently adhered to the backing can be prepared by laminating the releasably loaded elastomeric microspheres of a transfer tape to the backing. Tapes can also be double-coated tapes wherein both sides of the backing have a layer of releasably loaded elastomeric microspheres on them. Useful backing material include polymeric films, such as those made from cast and oriented polyesters, cast and oriented polypropylene, polyethylene, paper, metal foils, woven and nonwoven fabrics, and foams, such as those made from polyolefins and acrylics. Examples of suitable acrylic foams are those disclosed in U.S. Pat. No. 4,415,615. Suitable polyolefin foams include crosslinked polyethylene and polyethylene/EVA foams.

The releasably loaded elastomeric microspheres described also are useful for a sprayable composition. The preparation of such sprayable compositions are well-known in the art (see for example U.S. Pat. Nos. 3,691,140, 4,994,322, 5,118,750, 5,215,818 and 5,502,108). The spray process is safe, fast, less likely to contaminate ground water, results in lower exposure to the environment and other non-target species, and overall has lower labor costs.

The objects, features and advantages of the present invention are further illustrated by the following examples, but the particular materials and amounts thereof recited in these examples, as well as other conditions and details, should not be construed to unduly limit this invention. All materials are commercially available, for example from Aldrich Chemicals and known to those skilled in the art unless otherwise stated or apparent. In the examples, all parts and percentages are by weight, unless otherwise indicated. All molecular weights reported are number average molecular weight.

| Glossary | |
|---|---|
| AA | acrylic acid |
| AmA | ammonium acrylate |
| BDA | 1,4-butanediol diacrylate |
| IOA | isooctyl acrylate |
| NaSS | sodium styrene sulfonate |
| PEO750 | an acrylate terminated poly(ethylene oxide) polymer having an average molecular weight of 750 |

EXAMPLE 1

Example 1 illustrates the incorporation of an agriculturally active agent (E-11-tetradecenol) tacky, hollow elastomeric microspheres using an in-situ addition process. A 500 ml baffled reaction flask equipped with a stirrer, thermocouple, and nitrogen inlet was charged with a water phase containing 225.0 grams of deionized water and 3.0 grams of STEPANOL AMV surfactant (ammonium lauryl sulfate, 25% solids in water, available from Stepan). An oil phase consisting of 72.0 grams of isooctyl acrylate, 3.0 grams of acrylic acid, 3.76 grams of E-11-tetradecenol (available from Bedoukian Research Inc.) and 0.40 gram of dissolved LUCIDOL 75 initiator (75% active benzoyl peroxide available from Elf Atochem) was added to the reactor and the agitation set at 350 rpm. The dispersion was heated to 65° C. At 65° C., the reactor was degassed with nitrogen. A slight rise in temperature in the reaction was seen to 66° C. After eight hours at 65° C., the mixture was cooled, filtered and collected. Optical microscopy revealed hollow spherical particles having an average particle size of 74 micrometers. The theoretical releasable agriculturally active agent content of these microspheres was 5% by weight.

EXAMPLE 2

Example 2 illustrates the incorporation of an agriculturally active agent (E-11-tetradecenol) into tacky, small elastomeric microspheres using a post-polymerization addition process. A water phase was prepared by mixing 2280 grams of deionized water and 62.17 grams of STANDAPOL-A surfactant (ammonium lauryl sulfate, 25% solids in water, available from Henkel) in a 4000 ml beaker. An oil phase consisting of 1521.7 grams of isooctyl acrylate was added to the water phase, resulting in a white dispersion upon mixing. Mixing with an homogenizer (Model 15MR available from APV Gaulin) at 19,305 kPa (2800 psi) yielded monomer droplets having particle sizes less than 5 micrometers.

3586.4 grams of the white dispersion were transferred to a 4000 ml baffled reactor equipped with a stirrer, nitrogen inlet and temperature probe. The dispersion was heated to 65° C. Once at 65° C., 6.34 grams of LUCIDOL-75 initiator (75% active benzoyl peroxide available from Elf Atochem) was added and the mixture degassed. After a 45 minute induction, the reaction temperature increased to 80° C. The dispersion was cooled by an ice bath to 67° C. and a reaction temperature of 65° C. was maintained for four hours. After four hours, the mixture was cooled, filtered and collected. Optical microscopy revealed spherical particles having an average particle size of 5 micrometers.

Elastomeric microspheres having a theoretical releasable agriculturally active agent content of 10% by weight were prepared by adding 101.5 grams of this microsphere dispersion to 4.0 grams of E-11-tetradecenol (Available from Bedoukian Research Inc.) and mixing for eight hours. No visible changes in the dispersion were noted.

EXAMPLE 3

Example 3 illustrates the incorporation of an agriculturally active agent (E-11-tetradecenol) into non-tacky, solid elastomeric microspheres using an in-situ addition process. A 500 ml baffled reaction flask equipped with a stirrer, thermocouple, and nitrogen inlet was charged with a water phase containing 227.4 grams of deionized water and 0.85 gram poly(vinyl alcohol) polymeric stabilizer (87–89% hydrolyzed poly(vinyl alcohol) having a molecular weight –13,000–23,000 available from Aldrich Chemical). An oil phase consisting of 72.0 grams of isooctyl acrylate, 3.0 grams of acrylic acid, 1.5 grams 1,4-butanediol diacrylate crosslinking agent, 7.5 grams of E-11-tetradecenol (available from Bedoukian Research Inc.) and 0.40 grams of dissolved LUCIDOL 75 initiator (75% active benzoyl peroxide available from Elf Atochem) was added to the reactor and the agitation set at 400 rpm. The dispersion was heated to 65° C. At 65° C., the reactor was degassed with nitrogen. A slight rise in temperature in the reaction was seen to 66° C. After three hours at 65° C., the mixture was cooled, filtered and collected. Optical microscopy revealed solid spherical particles having an average particle size of 99 micrometers. The theoretical releasable agriculturally active agent content of these microspheres was 10% by weight.

EXAMPLE 4

Example 4 illustrates the incorporation of an agriculturally active agent (E-11-tetradecenal acetate) into non-tacky, solid elastomeric microspheres using an in-situ addition process. A water phase was prepared by mixing 228.5 grams of deionized water, 1.15 grams of sodium styrene sulfonate and 0.75 gram of SIPONATE DS-10 surfactant (sodium dodecylbenzenesulfonate available from Alcolac) in a 1000 ml beaker. An oil phase consisting of 51.32 grams of isooctyl acrylate, 7.5 grams acrylic acid, 15.01 grams of an acrylate terminated poly(ethylene oxide) polymer having an average molecular weight of 750, 0.76 gram 1,4-butanediol diacrylate crosslinking agent, 7.5 grams E-11-tetradecenal acetate (available from Bedoukin Research Inc.) and 0.40 gram LUCIDOL 75 initiator (75% active benzyl peroxide from Elf Atochem) was added to the water phase. The mixture was homogenized using a high shear mixer (Model 1 L, available from Gifford Wood ) for 15 minutes to obtain a fine emulsion of the oil phase (about 3–5 micron average particle size).

The dispersion was then transferred to a 500 ml baffled reaction flask equipped with a stirrer, thermocouple, and nitrogen inlet and the dispersion was mixed at 400 rpm. The dispersion was heated to 65° C. At 65° C., the reactor was degassed with nitrogen. A slight rise in temperature in the reaction was seen to 66° C. After three hours at 65° C., the mixture was cooled, filtered and collected. Optical microscopy revealed solid spherical particles having an average particle size of 1 micrometers. The theoretical releasable agriculturally active agent content of these microspheres was 10% by weight.

EXAMPLE 5

Example 5 illustrates the incorporation of an agriculturally active agent E-11-tetradecenal acetate) into tacky, hollow elastomeric microspheres using an in-situ addition process. A water phase was prepared by mixing 225.0 grams of deionized water, and 3.0 grams of STEPANOL AMV surfactant (ammonium lauryl sulfate, 25% solids in water, available from Stepan) in a 500 ml baffled reaction flask equipped with a stirrer, thermocouple, and nitrogen inlet. An oil phase consisting of 72.0 grams of isooctyl acrylate, 3.0 grams acrylic acid, 0.76 gram 1,4-butanediol diacrylate crosslinking agent, 3.75 grams E-11-tetradecenal acetate (available from Bedoukin Research Inc.) and 0.30 gram LUCIDOL 75 initiator (75% active benzoyl peroxide available from Elf Atochem) was added to the water phase.

The dispersion was mixed at 400 rpm and heated to 65° C. At 65° C., the reactor was degassed with nitrogen. A slight rise in temperature in the reaction was seen to 66° C. After sixteen hours at 65° C., the mixture was cooled, filtered and collected. Optical microscopy revealed solid spherical particles. The theoretical releasable agriculturally active agent content of these microspheres was 5% by weight.

EXAMPLE 6

Example 6 illustrates the incorporation of an agriculturally active agent (citronellal) tacky, hollow elastomeric microspheres using an in-situ addition process. A 500 ml baffled reaction flask equipped with a stirrer, thermocouple, and nitrogen inlet was charged with a water phase containing 225.0 grams of deionized water and 3.01 grams of STEPANOL AMV surfactant (ammonium lauryl sulfate, 25% solids in water, available from Stepan). An oil phase consisting of 72.0 grams of isooctyl acrylate, 3.0 grams of acrylic acid, 3.76 grams of citronellal (Aldrich Chemical) and 0.30 gram of dissolved LUCIDOL 75 initiator (75% active benzoyl peroxide available from Elf Atochem) was added to the reactor and the agitation set at 350 rpm. The dispersion was heated to 65° C. At 65° C., the reactor was degassed with nitrogen. A slight rise in temperature in the reaction was seen to 66° C. After 16 hours at 65° C., the mixture was cooled, filtered and collected. Optical microscopy revealed hollow spherical particles having an average particle size of 63 micrometers. The theoretical releasable agriculturally active agent content of these microspheres was 5% by weight.

Examples 7–11 demonstrate the synthesis of releasably loaded elastomeric microspheres containing undecanol. Although not an agriculturally active agent, undecanol is an analog model that incorporates into and releases from the elastomeric microspheres. As an analog model they have been found to effectively simulate the properties of the pheromones as used in Examples 1–6.

EXAMPLE 7

Example 7 illustrates the incorporation of undecanol into tacky, solid elastomeric microspheres using an in-situ addition process. A 1000 ml baffled reaction flask equipped with a stirrer, thermocouple, and nitrogen inlet was charged with a water phase containing 480 grams of deionized water, 6.4 grams acrylic acid and 4.48 grams of STANDAPOL-A surfactant (ammonium lauryl sulfate, 25% solids in water, available from Henkel). The water phase was neutralized to a pH>7.0 with ammonium hydroxide. An oil phase consisting of 313.6 grams of isooctyl acrylate, 32 grams undecanol (available from Aldrich Chemical) and 1.41 grams of dissolved LUCIDOL 75 initiator (75% active benzoyl peroxide available from Elf Atochem) was added to the reactor and the agitation set at 400 rpm. The dispersion was heated to 65° C. At 65° C., the reactor was degassed with nitrogen. A rise in temperature in the reaction was seen to 79° C. The mixture was cooled to 65° C. and the microspheres were filtered and collected. Optical microscopy revealed solid spherical particles having average particle sizes in the range of 20–90 micrometers. The theoretical releasable agriculturally active agent analog content of these microspheres was 10% by weight.

EXAMPLE 8

Example 8 illustrates the incorporation of undecanol into solid elastomeric microspheres using a post polymerization addition process. A 1000 ml baffled reaction flask equipped with a stirrer, thermocouple, and nitrogen inlet was charged with a water phase containing 450 grams of deionized water, 30 grams of a 10% solution of acrylic acid in water and 6.0 grams of STANDAPOL-A surfactant (ammonium lauryl sulfate, 25% solids in water, available from Henkel). The water phase was neutralized to a pH>7.0 with ammonium hydroxide. An oil phase consisting of 147 grams of isooctyl acrylate and 0.7 gram of dissolved LUCIDOL 75 initiator (75% active benzoyl peroxide available from Elf Atochem) was added to the reactor and the agitation set at 400 rpm. The dispersion was heated to 65° C. At 65° C., the reactor was degassed with nitrogen. After 22 hours at 65° C., the mixture was cooled, filtered and collected. Optical microscopy revealed solid spherical particles having an average particle size of 95 micrometers.

Elastomeric microspheres having a theoretical releasable agriculturally active agent analog content of 10% by weight were prepared by adding 6.8 grams of undecanol (available for Aldrich Chemical) to 272.5 grams of this microsphere dispersion and mixing overnight. No visible changes in the dispersion were noted.

COMPARATIVE EXAMPLE 1

Comparative Example 1 illustrates the incorporation of high loadings of undecanol into solid elastomeric microspheres using an in-situ addition process. A 1000 ml baffled reaction flask equipped with a stirrer, thermocouple, and nitrogen inlet was charged with a water phase containing 360 grams of deionized water, 4.8 grams acrylic acid and 3.4 grams of STANDAPOL-A surfactant (ammonium lauryl sulfate, 25% solids in water, available from Henkel). The water phase was neutralized to a pH>7.0 with ammonium hydroxide. An oil phase consisting of 235.2 grams of isooctyl acrylate, 48 grams undecanol (available from Aldrich Chemical) and 1.1 grams of dissolved LUCIDOL 75 initiator (75% active benzoyl peroxide available from Elf Atochem) was added to the reactor and the agitation set at 400 rpm. The dispersion was heated to 65° C. At 65° C., the reactor was degassed with nitrogen. A rise in temperature in the reaction occurred following degassing. During the exotherm, the reaction coagulated.

EXAMPLE 9

Example 9 illustrates the incorporation of undecanol into solid elastomeric microspheres using an in-situ addition process. A water phase was prepared by mixing 480 grams of deionized water, 6.4 grams of acrylic acid and 4.46 grams of STANDAPOL-A surfactant (ammonium lauryl sulfate, 25% solids in water, available from Henkel). The water phase was neutralized to a pH>7.0 with ammonium hydroxide. An oil phase consisting of 313.6 grams of isooctyl acrylate and 32 grams undecanol (available from Aldrich Chemical) was added to the water phase. Mixing with an homogenizer (Model 15MR available from APV Gaulin) at 19,305 kPa (2800 psi) yielded monomer droplets having particle sizes less than 5 micrometers.

621 grams of the dispersion was then transferred to a 1000 ml baffled reaction flask equipped with a stirrer, thermocouple, and nitrogen inlet and the dispersion was mixed at 400 rpm. 1.09 grams of LUCIDOL 75 initiator (75% active benzoyl peroxide available from Elf Atochem) was added to the reactor and the agitation set at 400 rpm. The dispersion was heated to 65° C. At 65° C., the reactor was degassed with nitrogen. A slight rise in temperature in the reaction was seen to 70° C. After four hours at 65° C., the mixture was cooled, filtered and collected. Optical microscopy revealed solid spherical particles having average particle sizes in the range of 1–10 micrometers. The theoretical releasable agriculturally active agent analog content of these microspheres was 10% by weight.

EXAMPLE 10

Example 10 illustrates the incorporation of undecanol into tacky, solid elastomeric microspheres using an in-situ addition process. A water phase was prepared by mixing 480 grams of deionized water, 3.2 grams sodium styrene sulfonate and 6.4 grams of STANDAPOL-A surfactant (ammonium lauryl sulfate, 25% solids in water, available from Henkel). An oil phase consisting of 236.8 grams of isooctyl acrylate, 32 grams acrylic acid, 48 grams of an acrylate terminated poly(ethylene oxide) polymer having an average molecular weight of 750 and 16 grams undecanol (available from Aldrich Chemical) was added to the water phase. Mixing with an homogenizer (Model 15MR available from APV Gaulin) at 19,305 kPa (2800 psi) yielded monomer droplets having particle sizes less than 5 micrometers.

591 grams of the dispersion was then transferred to a 1000 ml baffled reaction flask equipped with a stirrer, thermocouple, and nitrogen inlet and the dispersion was mixed at 400 rpm. 1.01 grams of LUCIDOL 75 initiator (75% active benzoyl peroxide available from Elf Atochem) was added to the reactor and the agitation set at 400 rpm. The dispersion was heated to 65° C. At 65° C., the reactor was degassed with nitrogen. After four hours at 65° C., the mixture was cooled, filtered and collected. Optical microscopy revealed solid spherical particles having an average particle size of 6 micrometers. The releasable agriculturally active agent analog content of these microspheres was 5% by weight.

Table 1 summarizes monomer compositions, solids content, releasably loaded agriculturally active agents or analogs, loading method, theoretical loading levels, particle sizes (when available) and presence of tack in the elastomeric microsphere product.

TABLE 1

| Ex. | Monomer Composition (% by weight) | Solids (%) | Active Agent/Analog | Method | Theoretical Loading | Size ($\mu$m) | Tack |
|---|---|---|---|---|---|---|---|
| 1 | IOA/AA (96/4) | 25 | E-11-tetradecenol | In-situ | 5 | 74 | Yes |
| 2 | IOA (100) | 40 | E-11-tetradecenol | Post Add | 10 | 5 | Yes |
| 3 | IOA/AA/BDA (96/4/2) | 25 | E-11-tetradecenol | In-situ | 10 | 99 | No |
| 4 | IOA/PEO750/AA/BDA/NaSS (68.5/20/10/1.5/1) | 25 | E-11 Tetradecanyl Acetate | In-situ | 10 | 1 | No |
| 5 | 96/4 IOA/AA | 25 | E-11 tetradecanyl Acetate | In-situ | 5 | — | Yes |

TABLE 1-continued

| Ex. | Monomer Composition (% by weight) | Solids (%) | Active Agent/Analog | Method | Theoretical Loading | Size (μm) | Tack |
|---|---|---|---|---|---|---|---|
| 6 | IOA/AA (96/4) | 25 | Citronella | In-situ | 5 | 63 | Yes |
| 7 | IOA/AmA (98/2) | 40 | Undecanol | In-situ | 10 | 20–90 | Yes |
| 8 | IOA/AmA (98/2) | 25 | Undecanol | In-situ | 10 | 95 | Yes |
| 9 | IOA/AmA (98/2) | 40 | Undecanol | In-situ | 10 | 1–10 | Yes |
| 10 | IOA/AA/PEO750/ NaSS (74/10/15/1) | 40 | Undecanol | In-situ | 5 | 6 | Yes |

Release Rate Measurements

The release rate of the agriculturally active agent from the releasably loaded elastomeric microspheres was determined by coating the microspheres onto a backing and extracting the active agent out of the microsphere at various time intervals. Samples were prepared by adding 1% UCAR Polyphobe 104 (alkali swellable associative thickener available from Union Carbide) to the microsphere suspension to adjust coating viscosity. These thickened suspensions were then knife-coated onto a chemically primed polyester at a 50 micrometer gap and oven dried at 65° C. for five minutes. A 10 cm×15 cm portion of the dried coated sample was placed in a known amount of heptane to extract the agriculturally active agent from the releasably loaded elastomeric microspheres. The heptane solution was then analyzed by gas chromatography to determine the amount of the extracted agriculturally active agent. As the agriculturally active agent was released from the microsphere, the concentration of the agriculturally active agent extracted by the heptane for a given sample decreased. The changes in the sample are recorded relative to a sample taken at time zero and the reflect the relative amount of the agent remaining in the microsphere.

TABLE 2

| Example | Time = 0 | Time = 1 hour | Time = 6 hour | Time = 24 hour |
|---|---|---|---|---|
| 5 | 1 | 0.98 | 0.94 | nd |
| 8 | 1 | 0.91 | 0.67 | 0.30 |
| 7 | 1 | 1.00 | 0.97 | 0.82 |
| 10 | 1 | 0.96 | 0.93 | 0.89 |

This invention is further illustrated by the following examples that are not intended to limit the scope of the invention. In the examples, all parts, ratios and percentages are by weight unless otherwise indicated. The following test methods were used to evaluate and characterize the low adhesion backsize compositions produced in the examples. All materials are commercially available, for example from Aldrich Chemicals, unless otherwise indicated or described.

What is claimed is:

1. A plurality of releasably loaded elastomeric microspheres wherein each releasably loaded elastomeric microsphere comprises an elastomeric microsphere and at least one releasable agriculturally active agent within the optical boundaries of the elastomeric microsphere in an amount sufficient to diffuse out of the elastomeric microspheres, wherein the elastomeric microspheres have an average particle size in the range of 0.5 to 300 micrometers.

2. The releasably loaded elastomeric microspheres according to claim 1, wherein the agriculturally active agent is an insecticide, a herbicide, a fungicide, a bacteriacide, a pheromone or other pesticide, an insect repellent or mixtures thereof.

3. The releasably loaded elastomeric microspheres according to claim 2, wherein the agriculturally active agent or mixture of agents is loaded into the elastomeric microspheres in an amount that is at least 1% by weight of the releasably loaded elastomeric microspheres.

4. The releasably loaded elastomeric microspheres according to claim 1, wherein the elastomeric microspheres are tacky elastomeric microspheres.

5. The releasably loaded elastomeric microspheres according to claim 1, wherein the elastomeric microspheres are hollow elastomeric microspheres.

6. The releasably loaded elastomeric microspheres according to claim 1, wherein the elastomeric microspheres are the suspension polymerization product of at least one free radically polymerizable polar monomer copolymerized with at least one vinyl ester monomer.

7. The releasably loaded elastomeric microspheres according to claim 1, wherein the elastomeric microspheres are elastomeric acrylate microspheres, elastomeric vinyl ester microspheres or mixtures thereof.

8. The releasably loaded elastomeric microspheres according to claim 1, wherein the elastomeric microspheres are the suspension polymerization product of at least one free radically polymerizable polar monomer copolymerized with at least one (meth)acrylic acid monomer.

\* \* \* \* \*

UNITED STATES PATENT AND TRADEMARK OFFICE
CERTIFICATE OF CORRECTION

PATENT NO.    : 6,471,975 B1
DATED         : October 29, 2002
INVENTOR(S)   : Banovetz, John P.

It is certified that error appears in the above-identified patent and that said Letters Patent is hereby corrected as shown below:

<u>Title page,</u>
Item [56], U.S. PATENT DOCUMENTS, "3,928,546" should read -- 3,928,564 --.

<u>Column 1,</u>
Line 40, delete "." following "organic".

Signed and Sealed this

Eleventh Day of November, 2003

JAMES E. ROGAN
*Director of the United States Patent and Trademark Office*